United States Patent [19]
Mouk et al.

[11] Patent Number: 5,616,821
[45] Date of Patent: Apr. 1, 1997

[54] METHODS FOR PURIFYING AND RECOVERING CONTAMINATED REFRIGERANTS WITH SOLUTIONS OF BASES IN ORGANIC SOLVENTS

[75] Inventors: Robert W. Mouk, Westerville; Albert E. Abel, Powell, both of Ohio

[73] Assignee: Commodore Laboratories, Inc., Columbus, Ohio

[21] Appl. No.: 377,631

[22] Filed: Jan. 30, 1995

Related U.S. Application Data

[63] Continuation-in-part of Ser. No. 207,286, Mar. 7, 1994, abandoned.

[51] Int. Cl.$^6$ .................................................. C07C 17/38
[52] U.S. Cl. ............................................. 570/177; 570/262
[58] Field of Search ........................................ 570/177, 262

[56] References Cited

FOREIGN PATENT DOCUMENTS 4205341  8/1993  Germany .

OTHER PUBLICATIONS

Downing Fluorocarbon Refrigerants Handbook (1988) Prentice–Hall pp. 177, 182–189, 302–303, 306–308.
Takao Heyashi Kogyo Kagaku Zasshi (1965) vol. 68, No. 10, 2002 +.

*Primary Examiner*—Alan Siegel
*Attorney, Agent, or Firm*—Howard M. Ellis

[57] ABSTRACT

Refrigerants, such as Freon® 12 and other potential ozone depleting substances will be in short supply as their production is phased out, and until existing refrigeration equipment is retrofitted to receive more environmentally friendly refrigerants. Existing supplies of such refrigerants when contaminated with other refrigerants especially chlorofluorohydrocarbons like Freon 22 form azeotropes, which are not readily separated by conventional distillation methods, are selectively decomposed in-situ by reacting with bases such as metal hydroxides in aqueous solutions or compatible organic solvents. The remaining non-reacted refrigerant-containing composition is readily recycled by separation and recovery methods from the reaction mixture to provide a reusable refrigerant composition practically free of contaminating refrigerant.

15 Claims, No Drawings

METHODS FOR PURIFYING AND RECOVERING CONTAMINATED REFRIGERANTS WITH SOLUTIONS OF BASES IN ORGANIC SOLVENTS

CROSS REFERENCE TO RELATED APPLICATION

This application is a continuation-in-part of application Ser. No. 207,286, filed Mar. 7, 1994 now abandoned.

TECHNICAL FIELD

The present invention relates generally to the reclamation of chlorofluorocarbons (CFCs), and more specifically, to methods of purifying and recovering refrigerants from refrigerant mixtures for recycling/reuse.

BACKGROUND OF THE INVENTION

Chlorofluorocarbons (CFCs) are synthetic chemical compounds widely used in refrigeration and air conditioning; as aerosol propellants and solvents; in forming foams, including those used in fast-food packaging; and in rigid insulation. Scientists now see these synthetic chemicals as the main threat to Earth's protective ozone layer. Because CFCs are immune to destruction in the troposphere, and because they eventually float upwardly, their manufacture and release have lead to the accumulation of large amounts in the stratosphere. In the stratosphere, CFCs are broken down by sunlight into chlorine, which has a catalytic and destructive effect on ozone. The result has been a significant decline in the global ozone shield and an increase in the amount of harmful ultraviolet radiation reaching the surface of Earth. According to a United Nations' study, every 1 percent drop in ozone will lead to a 3 percent increase in non-melanoma skin cancers in light-skinned people, as well as dramatic increases in cataracts, lethal melanoma cancers, and damage to the human immune system. Higher levels of UV light may also worsen ground-level pollution and hurt plants, animals, and especially light sensitive aquatic organisms.

As a result, destruction of CFCs, and in some instances, reclamation of CFC refrigerants is a vital component of the national and global strategies for protection of the earth's ozone layer in a manner consistent with minimal economic disruptions associated with the phase-out of this class of chemicals. There are still sizable reserves of CFCs on hand which must be treated and converted to environmentally benign substances. Likewise, until existing refrigeration and air conditioning equipment is replaced or retrofitted with devices which are capable of operating with more environmentally friendly refrigerants, as CFC production is curtailed and eventually eliminated, industry and consumers must rely increasingly on the availability of reclaimed refrigerants.

However, successful reclamation is presently hampered due to the occurrence of inadvertent contamination of refrigerants by other refrigerants. In order to qualify for reuse, reclaimed refrigerants are required to meet the American Refrigeration Institute's "700" specifications which stipulate the permissible levels of contaminants. That is, strict limits are placed on moisture, particulates, acidity, oil content, non-condensible gases, and other refrigerants present. Existing refrigeration and air conditioning equipment appears capable of employing reclaimed refrigerants. Existing reclamation processes are capable of meeting all of the foregoing criteria with the exception of "other refrigerants", which are not permitted to exceed 0.5 percent maximum.

One example of a widely found refrigerant mixture is Freon® 12, a trademark of E. I. DuPont, which is dichlorodifluoromethane, contaminated with Freon 22, which is chlorodifluoromethane, hereinafter called R-12 and R-22, respectively. Although removal of the unwanted R-22 contaminant from such a mixture would appear to be readily accomplished by distillation due to differences in their boiling points (R-12 b.p. −29.8° C. and R-22 b.p. −41° C.), separation by distillation is not readily achieved due to the formation of an azeotrope consisting of 75 percent R-22, when the two refrigerants become mixed.

Other known technologies for the destruction of CFCs such as thermal oxidation, catalytic decomposition, supercritical water oxidation, plasma destruction methods, biological processes, UV photolysis, and so on, are either in experimental stages of development, economically unattractive or incapable of selectively destroying the unwanted contaminating refrigerant without also eliminating the desired refrigerant.

Quite significantly, the present inventors discovered that solutions of a base, such as aqueous solutions sodium hydroxide and solutions of bases in organic solvents can be efficiently employed in highly economic processes of purifying contaminated refrigerant mixtures, including the recovery of purified refrigerant to readily meet the "other refrigerant" specification. Accordingly, the methods are especially useful in reclamation processes where production of certain CFCs, such as R-12 is being phased-out of production, but market demand remains strong.

The hydrolysis of chlorodifluoromethane (R-22) in aqueous sodium hydroxide was disclosed by Takao Hayashi in a paper entitled "Preparation of Sodium Formate by Hydrolysis of Chlorodifluoromethane", *Kogyo Kagaku Zasshi*, Vol. 68, No. 10, 2002 (1965). The studies were conducted with R-22 having a minimum specification of 99.9% $CHClF_2$, 0.4% $CCl_2F_2$ and 0.3% air. However, the R-22 reactant actually used in these studies was analyzed by gas chromatography to verify the compositional make-up. According to the author, apparently no refrigerant was detected other then the R-22 reactant. That is to say, while the R-22 refrigerant cylinder specification had allowed for a trace amount (0.4%) R-12, chromatographic analysis showed that none was found in the refrigerant reactant used in the studies.

Hayashi concluded that since it was apparently known that "dichlorodifluoromethane is not easily susceptible to being hydrolyzed, it seems that protonic hydrogen atom may make easy the hydrolysis of chlorodifluoromethane." The only objective of the Hayashi paper was to demonstrate the successful production of sodium formate by alkaline hydrolysis of chlorodifluoromethane (R-22), which was free of other refrigerant reactants. In addition, the earlier efforts of Hayashi did not include separation and recovery steps in order to retrieve a purified refrigerant, like R-12.

R. C. Downing in *Fluorocarbon Refrigerant Handbook*, Prentice Hall, 1988 (307–308) describes a series of studies in which R-22 alone and with R-12 was bubbled through solutions of sodium methylate in methanol. Downing disclosed the lack of stability and breakdown of R-22 which could be detected by the formation of a sodium chloride precipitate. The author reported R-12 was not similarly effected. In testing mixtures of R-12 and R-22 alcoholic sodium methylate the presence of R-22 at concentrations down to 5 wt percent was detected. In conducting his stability/analytical studies Downing failed to teach or suggest steps for recovering the more stable R-12 from refrigerant mixtures after treating with the base as a viable means in recycling refrigerants.

Accordingly, the methods disclosed herein effectively overcome the dilemma of reclamation of refrigerants containing more than 0.5 percent "other refrigerant." Methods heretofore failed either to recognize the ability of recovering useful refrigerants from contaminated mixtures, or were ineffective in selectively removing the contaminating refrigerant. With insufficient quantities of newly produced perhalogenated refrigerants like R-12 available to dilute hydrochloro-fluorocarbon refrigerants to acceptable levels, and environmental regulations prohibiting venting to the atmosphere the only readily available alternative has been costly incineration. This, however, does not allow for reclamation.

SUMMARY OF THE INVENTION

The term "refrigerant" as used throughout the specification and claims is a generic term intended to mean fluorocarbon compounds as a class of chemicals which are suitable for use in refrigeration and air conditioning equipment, but may also have other applications. The term thus embraces halofluorocarbons and halofluorohydrocarbons, such as chlorofluorocarbons (CFCs), bromofluorocarbons, chlorofluorohydrocarbons, and so on. Likewise, the term "refrigerant" is also intended to include fluorocarbons which are useful as solvents, aerosol propellants, in manufacturing synthetic foams, packaging, insulation, retardant compounds for fire extinguishers, and the like. Thus, it should be understood "refrigerant" is intended to embrace a broader range of compounds then merely those which are suitable for air conditioning and refrigeration applications. They include products commercially available under trademarks, such as Freon, Halon, Frigen, Arcton, Genetron and Isotron.

In accordance with the invention useful methods are provided for purifying refrigerant compositions through dehalogenation reactions allowing for the selective destruction of contaminating refrigerants, usually fluorohydrocarbon refrigerants while also allowing for recycling/reuse of commercially important refrigerants.

The purification methods disclosed herein include the steps of:

(a) providing a composition comprising at least two refrigerants (i) a perhalogenated refrigerant compound and (ii) a contaminating fluoroalkane refrigerant compound having at least one hydrogen atom and at least one other halogen atom in addition to fluorine, e.g. chlorine, bromine and/or iodine;

(b) reacting the composition of step (a) with an aqueous solution of a base to selectively decompose the contaminating fluoroalkane refrigerant compound (ii), and (c) recovering the refrigerant composition from the reaction mixture of step (b), the composition comprising the perhalogenated refrigerant compound (i), the recovered composition being sufficiently free of the contaminating fluoroalkane refrigerant compound (ii) to enable recycling/reuse.

Quite significantly, it was discovered that refrigerant mixtures, like azeotropes, such as dichlorodifluoromethane contaminated with chlorodifluoromethane, and other refrigerant mixtures which are not azeotropes but have similar boiling points as to make separation by distillation difficult, can be effectively purified and separated by the methods disclosed herein. The separated and recovered refrigerants meet ARI 700 specifications for "other refrigerants."

Thus, the invention also contemplates methods of purifying refrigerant compositions by the steps of:

(a) providing a composition comprising at least two refrigerants: (i) a refrigerant selected from the group consisting of an azeotrope and a mixture of refrigerants having similar boiling points and (ii) a contaminating fluoroalkane refrigerant compound having at least one hydrogen atom and at least one other halogen atom in addition to fluorine;

(b) reacting the composition of step (a) with an aqueous solution of a base to selectively decompose the contaminating fluoroalkane refrigerant compound (ii), and (c) recovering the refrigerant composition from the reaction mixture of step (b), the refrigerant composition comprising the azeotrope or mixture of refrigerants having similar boiling points (i), the recovered composition being sufficiently free of said contaminating refrigerant compound (ii) to enable recycling/reuse.

Fluoroalkane as recited herein is intended to include halofluorohydrocarbons having at least one hydrogen atom and at least one other halogen atom in addition to fluorine, i.e., chlorine, bromine and/or iodine. More preferably, fluoroalkane refrigerants are halofluorohydrocarbons with<4 carbon atoms, and still more preferably, compounds having 1 or 2 carbon atoms.

As a further embodiment, the invention also includes methods of purifying refrigerant compositions with bases dissolved in organic solvents. This method of purification includes the steps of:

(a) providing a composition having at least two refrigerants, (i) a primary perhalogenated refrigerant compound and (ii) a contaminating fluoroalkane refrigerant compound having at least one hydrogen atom and at least one other halogen atom in addition to fluorine;

(b) reacting the composition of step (a) with a base in a suitably compatible organic solvent to selectively decompose the contaminating fluoroalkane refrigerant compound (ii), and (c) recovering a refrigerant composition from the reaction mixture of step (b), the composition comprising the primary perhalogenated refrigerant compound (i), the recovered composition being sufficiently free of the contaminating fluoroalkane refrigerant compound (ii) to enable recycling/reuse.

The primary perhalogenated refrigerant compound (i) is a halofluorocarbon usually containing at least one other halogen atom, such as chlorine and bromine, in addition to fluorine and the contaminating fluoroalkane refrigerant compound (ii) is usually a fluoromethane type.

This additional embodiment is especially useful in the decontamination of refrigerants where the composition comprises at least two refrigerants having similar boiling points or where an azeotrope has formed.

Most preferably, in each of the foregoing embodiments methods of purification relate to primary perhalogenated refrigerants (i) which are chlorofluorocarbons (CFCs) contaminated with fluoroalkane refrigerants (ii) which are usually chlorofluorohydrocarbon compounds.

DESCRIPTION OF THE PREFERRED EMBODIMENTS

Methods of the invention encompass the purification of compositions containing useful primary refrigerants. Expressions such as "primary refrigerant" and "primary perhalogenated refrigerant" as disclosed and claimed herein are used to denote the specific refrigerant(s) desired for recovery from contaminated refrigerant mixtures in the purification process. Primary refrigerants include mainly refrigerants which are perhalogenated, or in other words, refrigerant compounds in which all the carbons are fully substituted with halogen atoms. They include such representative examples as Freon® 11 (fluorotrichloromethane), Freon 12 (dichlorodifluoromethane), Freon 13 (chlorotrifluoromethane), Freon 14 (tetrafluoromethane), Freon 13B1 (bromotrifluoromethane), and so on. Thus, the foregoing expressions are intended to include mainly refrigerants which contain at least one other halogen atom in addition to fluorine, i.e., chlorine, bromine and iodine having up to four carbon atoms.

The expression "other refrigerant" is used herein to denote the contaminating refrigerant to be eliminated from refrigerant compositions containing the primary refrigerant. The methods are useful in purifying refrigerant compositions usually contaminated with>0.5 percent of other refrigerant. However, methods of the present invention are also effective in treating compositions containing minor or even trace amounts, i.e.,<0.5 percent other refrigerant(s). Primary refrigerant compositions either through manufacturing or other processing become contaminated with other refrigerants, particularly fluoroalkane refrigerant compounds having at least one hydrogen atom and at least one halogen atom in addition to their fluorine atom(s), which halogen atoms may be chlorine, bromine and/or iodine. The term "fluoroalkane" is intended to include mainly fluoromethane type refrigerant compounds, but also fluoroethanes. Specific representative examples of fluoromethane type other refrigerants include, but are not limited to FC-21 (fluorodichloromethane), FC-22 (chlorodifluoromethane), FC-21B1 (bromochlorofluoromethane), etc. Other fluoroalkane refrigerants include, for instance, 1,1,2,2-tetrachloro-2-fluoroethane (FC-121); 1,1,1-trifluoro-2,2-dichloroethane (FC-123).

Hence, the principal objective of the invention is the selective chemical decomposition or destruction of other refrigerants in compositions of refrigerant mixtures without decomposing the primary refrigerant. The invention comprises as a further principal objective the steps of separation and recovery of the composition containing the primary refrigerant from an aqueous or organic solvent reaction medium in a refined or purified state free or virtually free of other refrigerant, so as to meet American Refrigeration Institute specifications for other refrigerants. The methods enable recycling/reuse of discontinued or potentially scarce refrigerant compounds.

While the methods of the invention are especially useful in the reclamation of contaminated perhalomethane type primary refrigerants the invention contemplates the purification and recovery of other perhaloalkane primary refrigerants as well, such as the fluoroethanes and fluorobutanes. Representative examples include fluorocarbon or FC-112 (1,1,2,2-tetrachloro-1,2-difluoroethane), FC-113 (1,1,2-trichloro-1,2,2-trifluoroethane), and the like.

In addition to the reclamation of refrigerant compositions comprising a single perhalogenated primary refrigerant contaminated with other refrigerant(s), the invention contemplates the purification of refrigerant mixtures having similar boiling points, and particularly azeotrope refrigerants, like Freon 500 (dichlorodifluoromethane and 2,2-difluoroethane), Freon-503 (trifluoromethane and chlorotrifluoromethane), and particularly an azeotrope of dichlorodifluoromethane in which chlorodifluoromethane is the "other refrigerant."

The purification methods provide for the step of reacting a primary refrigerant-containing composition contaminated with other refrigerant, with an aqueous solution of a base or with a base in a suitably compatible organic solvent to selectively decompose the contaminating other refrigerant.

The expression "aqueous solution of a base" or variations similar thereto, as used in the specification and claims is intended to mean virtually any base having $pK_b$ in a range from about <0 to 7 wherein the base is the solute and water is the solvent therefor. The expression is not intended to include solutions of base wherein water is present in only minor amounts or present as an impurity. In practice, the aqueous solutions of base typically contain from about 3 to about 25 percent by weight base for those bases which are solids prior to dissolution. On the other hand, for bases which are liquids prior to mixing with water, aqueous solutions of bases can be prepared having considerably higher concentrations, i.e, up to about 95 percent. Representative examples of stronger bases at the lower end of the $pK_b$ range include alkali metal hydroxides, e.g., sodium, potassium and lithium hydroxides; alkaline earth metal hydroxides, e.g., calcium and magnesium hydroxides, and mixtures of metal hydroxides. Representative examples of weaker bases at the upper end of the $pK_b$ range include alkali metal and alkaline earth metal carbonates and bicarbonates, such as sodium, potassium, calcium and magnesium carbonates, bicarbonates and mixtures thereof. Other representative examples of useful bases are the quaternary ammonium bases, like tetramethylammonium and cetyltrimethylammonium hydroxides.

The reaction of the aqueous solution of base with the contaminated refrigerant composition comprising primary and other refrigerants is performed in a closed pressure vessel at temperatures generally in the range of about 5° C. to about 80° C. It will be recognized the process may be conducted at higher and lower temperature conditions than previously mentioned. At temperatures below 5° C. the rate of reaction of other refrigerant and base becomes reduced. While the rate of reaction at temperatures above 80° C. will be accelerated, pressure specifications of the reaction vessel will ultimately dictate the upper end of the reaction temperature range.

The process may be either batch or continuous. Conducting the reaction with an aqueous solution of a base, potassium hydroxide for instance, results in the formation of such by-products as potassium formate, potassium salts of fluorine, chlorine, bromine and iodine, depending on the particular other refrigerant present. Advantageously, salt by-products of the purification reaction, such as potassium fluoride, potassium chloride and potassium formate, are only soluble in the aqueous phase of the reaction mixture allowing for recovery of a purified refrigerant composition containing primary refrigerant substantially free of other refrigerants, and other unwanted by-products, like the salts previously mentioned.

Significantly, it was found that a "clean" separation and recovery of the primary refrigerant-containing composition from the aqueous reaction mixture is achieved by allowing the reaction mixture to remain in a quiescent state after mixing. With completion of the decomposition reaction the reactor mixer is deactivated. Advantageously, the limited miscibility of the primary refrigerant-containing composition in the aqueous solution of base allows the reaction mixture to separate into two distinct liquid phases: an upper aqueous phase, and lower refrigerant phase containing the primary refrigerant. This enables separation and recovery of the primary refrigerant-containing composition to be especially convenient where in most instances the need for further processing to recover substantially pure primary refrigerant can be avoided. That is, it was found the lower refrigerant phase can be readily separated from the upper aqueous layer or phase by withdrawing as a liquid from the bottom of the reaction vessel. Any residual solid salt byproducts in the lower refrigerant phase can be removed by means of an in-line filtration device of known design.

As a further aspect of the inventive process, it was discovered that dehalogenation of other refrigerants results in formation of reaction by-products, like sodium formate, sodium chloride and sodium fluoride. As the other refrigerant is dehalogenated base is depleted from the reaction mixture, and must be replenished. Simultaneously, reaction by-products are building-up in the aqueous reaction mixture. Although sodium fluoride is relatively insoluble in the aqueous reaction mixture, sodium formate and sodium chloride are fairly soluble, making separation of a large portion of the by-products from the aqueous phase of the reaction mixture more difficult.

However, it was found that by adding sodium hydroxide, for instance, to the aqueous phase of the reaction mixture to replenish the base, the greater solubility of the sodium hydroxide in water causes the less soluble salt by-products, i.e., formates, fluorides, bromides, chlorides, etc., to salt-out or precipitate from the "heel" of the reactor. Hence, it has been found that the reactor by-products can be conveniently and efficiently separated from the aqueous reaction mixture by means of replenishing the aqueous solution of base. Removal of the precipitated salts in turn can be effectuated by filtration means using methods within the purview of one having ordinary skill in the art.

The second embodiment of the purification process is also conducted with bases, but performed in a medium comprising "suitably compatible organic solvents." This expression or variations thereof appearing in the specification and claims are intended to denote (i) an organic solvent which is stable and non-reactive in the presence of the base and refrigerant, and (ii) the base is sufficiently soluble in the solvent to react with the contaminating fluoroalkane refrigerant to cause it to decompose. This would preferably include polar organic solvents, including monohydroxy alcohols, such as methyl and ethyl alcohols, tert-butyl alcohol, and so on. Other suitably compatible organic solvents would include the polyhydric alcohols, such as ethylene and propylene glycols. Certain ethers like ethyl ether can be used provided the base is sufficiently soluble therein. Other useful organic solvents include those derived from cyclic or linear mono and polyhydroxy alcohols and would include such representative examples as 2-ethoxyethanol; polyglycol ethers from the family of mono and dialkyl ethers of ethylene glycol, such as ethylene glycol monobutyl ether and the group of mono and dialkyl ethers of diethylene glycol, such as diethylene glycol monobutyl ether. These mono and polyhydroxy ethers are available under such trademarks as Cellosolve® and Carbitol®. Cyclic ether solvents, such as tetrahydrofuran would also be useful. Ester solvents like ethyl acetate may be used with bases provided they are not hydroxy bases like potassium hydroxide which will react with the solvent. Instead, an alkoxide base may be employed, such as sodium methoxide, sodium ethoxide, and so on.

It will be understood that certain solvents, such as reagent grade methyl and ethyl alcohols containing small amounts of water are intended to be included within the framework of the invention as disclosed and claimed herein.

As in the case of the aqueous system, the purification methods providing for treatment of a refrigerant composition in a media comprising an organic solvent may utilize most any base, especially strong bases, which are either liquids or solids prior to addition to the solvent, and may include inorganic bases such as metal hydroxides, and organic bases, such as metal alkoxides. It should be understood, however, the invention is not limited to hydroxides and alkoxides, but may be practically any substance that provides a pair of electrons for a covalent bond with a Lewis acid, and which is stable and sufficiently soluble or miscible in the organic solvent to react with and decompose the contaminating fluoroalkane refrigerant compound.

Generally, in decontaminating a refrigerant composition with a base in an organic solvent the method is conveniently performed in a pressure vessel of conventional design. Remaining primary refrigerants, like dichlorodifluoromethane can be recovered from the reaction mixture under reduced pressure while simultaneously warming the reaction vessel and condensing the gases by conventional compression or condensing methods, well known among persons skilled in this art.

The following specific examples demonstrate the various embodiments of the invention, however, it is to be understood they are for illustrative purposes only and do not purport to be wholly definitive as to conditions and scope.

EXAMPLE I

In order to demonstrate the recovery of perhalogenated CFCs from a mixture of refrigerants, a laboratory scale purification system was assembled. The system included a reactor consisting of a 14 liter stainless steel autoclave fitted with inlets/outlets to permit the addition of reactants and removal products. Vaporized products were withdrawn from the head space at the upper portion of the reactor, whereas liquid phases were withdrawn from outlets in the central and lower regions of the reactor. The reactor was equipped with a 1725 rpm Lignin mixer driving a 3 inch, 3 blade propeller with the stirrer shaft entering the reactor through a seal at the top of the reactor. A sight glass provided visual inspection of the reactor contents. Reactor temperature was regulated by an external jacket.

The reactor was evacuated and the vacuum used to draw in 7.1 liters of a 12.5 percent by weight aqueous solution of sodium hydroxide. A refrigerant mixture was analyzed according to ARI standard 700-93 specification using a Hewlett-Packard HP 5840A gas chromatograph and thermal conductivity detector. The refrigerant mixture was found to consist of 95.27 percent dichlorodifluoromethane (R-12), 4.45 percent chlorodifluoromethane (R-22), 0.11 percent air and 0.17 percent other impurities.

The contents of the reactor were stirred and cooled to −7.3° C. by means of a mixture of dry ice and isopropanol in the reactor jacket. This permitted direct transfer of the above mixed liquid refrigerant from the storage cylinder to the reactor by pressure difference. By the time the addition was complete the reactor had cooled further to −11° C. The coolant from the reactor jacket was drained and replaced with hot water, bringing the reactor to a maximum temperature of 38° C. and pressure of 138 psig during the run. When the reactor contents reached 25° C., one half hour after the refrigerant addition was complete, the time was noted.

Samples were collected at 15 minute intervals (actual stirring time). Sample collection procedure consisted of stopping the stirrer and allowing the reaction mixture to separate into a liquid refrigerant phase at the bottom of the reactor, and an upper aqueous liquid phase above the lower refrigerant phase, and then withdrawing a sample of the liquid refrigerant phase from the bottom of the reactor. This protocol was performed to obtain a more accurate and representative sampling of the treated refrigerant composition. Until the R-22 refrigerant level was reduced to specification levels of <0.5 percent the reaction was allowed to continue. This method also isolated the more volatile R-22 vapor in the head space of the reactor keeping it from recontaminating the liquid refrigerant phase at the bottom of the reactor, and thereby functioned as a barrier. In addition, caustic soda in the intermediate aqueous phase provided a further useful function by dehalogenating R-22 refrigerant in the upper vapor phase which might have liquified and recontaminate the refrigerant phase at the bottom of the reactor.

TABLE 1

| Time (minutes) | R-22 (%) |
| --- | --- |
| 15 | 1.85 |
| 30 | 0.85 |
| 60 | 0.17 |

The final analysis of the refrigerant phase at 60 minutes into the run showed ARI 700 specifications for other refrigerants being met with R-12=99.57 percent; R-22 other refrigerant=0.17 percent; air, water and other trace impurities=0.26 percent.

EXAMPLE II

A further experiment was conducted with the same refrigerant mixture used in Example I. The reactor was evacuated and the vacuum applied to withdraw 7.1 liters of 12.5 percent of the aqueous sodium hydroxide solution. The reaction was conducted using the same system as in Example I, except the refrigerant mixture (10.5 pounds) was charged to the reactor with an Applied Research Laboratories ReKlame® refrigerant recovery and recycle system. The refrigerant was withdrawn from the cylinder and added to the reactor as a liquid. Hot water was added to the reactor jacket, heating reactor contents to 42° C., and at a reactor pressure of 145 psig. After addition of the refrigerant mixture was completed the stirrer was deactivated, and the reaction mixture allowed to settle into a lower liquid refrigerant phase and an upper or intermediate aqueous phase. A refrigerant sample was withdrawn from the bottom of the reactor, and the reaction was allowed to continue for a period of one hour with additional samples withdrawn in the same manner from the same phase at 15 minute intervals and analyzed for other refrigerant. The analyses are provided in Table 2 below:

TABLE 2

| Time (minutes) | R-22 (%) |
| --- | --- |
| 0 | 1.87 |
| 15 | 0.60 |
| 30 | 0.11 |
| 45 | 0.02 |
| 60 | <0.01 |

The final analysis of the refrigerant phase at 60 minutes into the run showed ARI 700 specifications for other refrigerants being met with R-12=99.01 percent; R-22 other refrigerant=<0.01 percent; air, water and other trace impurities 0.98 percent.

EXAMPLE III

In order to demonstrate the selective dehalogenation and destruction of halofluorohydrocarbon refrigerants with solutions of bases in organic solvents a further experiment was performed using a monohydric alcohol as the solvent. A glass pressure resistant reaction flask was initially charged with 114 grams of diethylene glycol monomethyl ether commercially available from Union Carbide Corp., under the trademark Methyl Carbritol®. 3.1 grams of solid KOH was added to the reaction flask. The KOH dissolved completely in the solvent. A refrigerant mixture composed of 83.7 percent-by-weight dichlorodifluoromethane (Freon® 12/R-12) and 16.3 percent-by-weight chlorodifluoromethane (Freon 22/R-22) was charged to the KOH-containing solution. The solution was stirred at room temperature and gases in the headspace were drawn off and analyzed periodically by gas chromatography. Because of the greater volatility of the R-22 relative to the R-12, gases in the headspace are richer in the R-22 chlorofluorohydrocarbon component. Hence the analytical data in the following table correlates conservatively with the actual analysis of the liquified refrigerant:

TABLE 3

| Reaction Time | % R-12 | % R-22 |
| --- | --- | --- |
| 0 (start) | 77.2 | 22.2 |
| 20 minutes | 97.7 | 1.6 |
| 4 days (no stirring) | 99.3 | 0.4 |
| 5 days (stirring) | 99.5+ | not detectable |

The reaction flask was warmed and the refrigerant collected in a second flask and cooled in dry ice/isopropyl alcohol bath. The purified R-12 was recovered in greater than 75 percent yield, and had no detectable R-22 contaminant.

EXAMPLE IV

A further experiment was performed in the purification of refrigerant mixtures to demonstrate the selective dehalogenation and destruction of halofluoro-hydrocarbons with solutions of bases in organic solvents. A pressure resistant flask was first charged with 150.4 grams of tetraethylene glycol, a diol. 30.1 grams of solid NaOH was added to the organic solvent. The base was only sparingly soluble in the solvent. Even after heating much undissolved NaOH remained. 32.9 grams of a refrigerant mixture composed of 83.7 percent-by-weight dichlorodifluoromethane (R-12) and 16.3 percent-by-weight chlorodifluoromethane (R-22) was charged to the NaOH-organic solvent containing solution. The mixture was stirred at room temperature. Gases in the headspace were drawn off and analyzed periodically by gas chromatography. The following Table provides the results of this purification experiment:

TABLE 4

| Reaction Time | % R-12 | % R-22 |
| --- | --- | --- |
| 45 minutes | 77.5 | 21.5 |
| 2 hours | 82.6 | 16.4 |
| 4 hours | 90.7 | 8.4 |
| 23 hours | 95.2 | 3.0 |
| 30 hours | 98.7 | 0.6 |
| 48 hours | 97.5 | 0.1 |

At the completion of 48 hours the level of contaminating R-22 refrigerant was reduced to within acceptable limits for other refrigerant for recycling the R-12 refrigerant.

While the invention has been described in conjunction with specific examples thereof, they are illustrative only.

Accordingly, many alternatives, modifications and variations will be apparent to persons skilled in the art in light of the foregoing description, and it is therefore intended to embrace all such alternatives, modifications and variations as to fall within the spirit and broad scope of the appended claims.

We claim:

1. A method of purifying a refrigerant composition, which comprises the steps of:
   (a) introducing into a closed vessel a base in a suitably compatible organic solvent selected from the group consisting of polyhydric alcohol, polyglycol ether, monohydroxy ether and polyhydroxy ether;
   (b) introducing into the closed vessel of step (a) a refrigerant composition to form a reaction mixture with said suitably compatible organic solvent, said refrigerant composition comprising (i) a primary perhalogenated refrigerant compound and (ii) a contaminating fluoroalkane other refrigerant compound in an amount>0.5 percent-by-weight, said contaminating fluoroalkane other refrigerant compound having at least one hydrogen atom and at least one other halogen atom in addition to fluorine;
   (c) mixing the reaction mixture under elevated pressure to selectively decompose said contaminating fluoroalkane other refrigerant compound (ii) while allowing the temperature of said reaction mixture to warm, and
   (d) withdrawing the primary perhalogenated refrigerant compound (i) as a gas from said closed vessel with a sufficiently reduced amount of contaminating fluoroalkane other refrigerant compound (ii) to enable reuse in refrigeration and air conditioning equipment.

2. The purification method of claim 1 wherein the suitably compatible organic solvent is ethylene glycol, propylene glycol, ethylene glycol monobutyl ether or diethylene glycol monobutyl ether.

3. The purification method of claim 1 wherein the refrigerant composition of step (b) introduced into the closed vessel is a used refrigerant.

4. The purification method of claim 1 wherein the primary perhalogenated refrigerant withdrawn from said vessel comprises<0.5 percent-by-weight of said contaminating fluoroalkane other refrigerant compound.

5. The purification method of claim 1 wherein said primary perhalogenated refrigerant compound (i) comprises at least one other halogen atom in addition to fluorine and said contaminating fluoroalkane refrigerant (ii) is a fluoromethane type.

6. The purification method of claim 5 wherein the fluoromethane refrigerant is a member selected from the group consisting of chlorodifluoromethane, fluorodichloromethane, chlorofluoromethane, bromofluoromethane, bromodifluoromethane and mixtures thereof.

7. The purification method of claim 1 wherein the composition of step (b) is an azeotrope.

8. The purification method of claim 1 wherein the composition of step (b) comprises a mixture of at least two refrigerants having similar boiling points.

9. The purification method of claim 1 wherein the base is a strong base.

10. The purification method of claim 9 wherein the strong base is a hydroxide or alkoxide of a metal selected from the group consisting of alkali metals and alkaline earth metals.

11. The purification method of claim 5 wherein the base is a strong base.

12. The purification method of claim 11 wherein the strong base is a hydroxide or alkoxide of a metal selected from the group consisting of alkali metals and alkaline earth metals.

13. The purification method of claim 1 wherein the base and suitably compatible organic solvent of step (a) comprises an alkali metal hydroxide which is sufficiently soluble in said organic solvent to decompose the contaminating fluoroalkane refrigerant compound (ii) of the refrigerant composition of step (b) and the solvent is stable in the presence of said base.

14. The purification method of claim 7 wherein the azeotrope of step (b) comprises dichlorodifluoromethane and chlorodifluoromethane.

15. The purification method of claim 1 wherein the primary perhalogenated refrigerant (i) of step (b) is a chlorofluorocarbon and the contaminating fluoroalkane refrigerant (ii) of step (b) is a chlorofluorohydrocarbon.

* * * * *